(12) United States Patent  (10) Patent No.: US 8,394,116 B2
Kota et al.  (45) Date of Patent: Mar. 12, 2013

(54) SURGICAL TOOLS AND COMPONENTS THEREOF

(75) Inventors: Sridhar Kota, Ann Arbor, MI (US); Froukje Ellen Euwe, Utrecht (NL)

(73) Assignee: The Regents of The University of Michigan, Ann Arbor, MI (US)

( * ) Notice: Subject to any disclaimer, the term of this patent is extended or adjusted under 35 U.S.C. 154(b) by 786 days.

(21) Appl. No.: 12/424,032

(22) Filed: Apr. 15, 2009

(65) Prior Publication Data

US 2010/0042104 A1  Feb. 18, 2010

Related U.S. Application Data

(60) Provisional application No. 61/044,957, filed on Apr. 15, 2008.

(51) Int. Cl.
 *A61B 17/32* (2006.01)
(52) U.S. Cl. ............ 606/170; 606/79; 606/80; 606/167; 606/168; 606/169; 606/171; 606/172
(58) Field of Classification Search .............. 606/79–80, 606/167–172
See application file for complete search history.

(56) References Cited

U.S. PATENT DOCUMENTS

| | | | | |
|---|---|---|---|---|
| 4,541,423 A * | 9/1985 | Barber | ............................ | 606/80 |
| 4,941,466 A * | 7/1990 | Romano | ........................... | 606/80 |
| 5,505,737 A * | 4/1996 | Gosselin et al. | ................ | 606/79 |
| 5,695,513 A * | 12/1997 | Johnson et al. | ............... | 606/180 |
| 6,168,599 B1 * | 1/2001 | Frieze et al. | .................... | 606/80 |
| 6,337,142 B2 * | 1/2002 | Harder et al. | ................. | 428/573 |
| 6,780,175 B1 * | 8/2004 | Sachdeva et al. | ............. | 604/531 |
| 7,118,574 B2 * | 10/2006 | Patel et al. | ....................... | 606/80 |
| 7,413,543 B2 * | 8/2008 | Banik et al. | .................... | 600/129 |
| 7,503,920 B2 * | 3/2009 | Siegal | .............................. | 606/79 |
| 7,585,300 B2 * | 9/2009 | Cha | .................................. | 606/80 |
| 7,618,428 B2 * | 11/2009 | O'Quinn et al. | .............. | 606/159 |
| 7,632,275 B2 * | 12/2009 | Williams et al. | ............... | 606/80 |
| 7,846,162 B2 * | 12/2010 | Nelson et al. | ................... | 606/62 |
| 7,914,533 B2 * | 3/2011 | Nelson et al. | ................... | 606/64 |
| 7,942,875 B2 * | 5/2011 | Nelson et al. | ................... | 606/63 |
| 7,959,634 B2 * | 6/2011 | Sennett | ........................... | 606/79 |
| 2003/0083681 A1 * | 5/2003 | Moutafis et al. | .............. | 606/167 |
| 2004/0106940 A1 * | 6/2004 | Shaolian et al. | .............. | 606/170 |
| 2004/0147934 A1 * | 7/2004 | Kiester | ........................... | 606/80 |
| 2005/0075538 A1 * | 4/2005 | Banik et al. | ................... | 600/141 |
| 2005/0154262 A1 * | 7/2005 | Banik et al. | ................... | 600/179 |
| 2005/0165420 A1 * | 7/2005 | Cha | ................................. | 606/150 |
| 2005/0197536 A1 * | 9/2005 | Banik et al. | ................... | 600/179 |
| 2005/0216018 A1 * | 9/2005 | Sennett | ........................... | 606/79 |
| 2005/0222499 A1 * | 10/2005 | Banik et al. | ................... | 600/132 |

(Continued)

OTHER PUBLICATIONS

Tuijthof, G., et al, "A Compliant Instrument for Arthroscopic Joint Fusion", Proceedings of the DETC, ASME Design Engineering Technical Conferences and Computers and Information in Engineering Conference, Salt Lake City, Utah, 2004.

*Primary Examiner* — David Isabella
*Assistant Examiner* — Jacqueline Woznicki
(74) *Attorney, Agent, or Firm* — Harness, Dickey & Pierce, P.L.C.

(57) ABSTRACT

A surgical tool and monolithic frame therefore are disclosed. The monolithic frame defines a longitudinal axis between opposite first and second ends thereof, and is adapted to receive the flexible drive shaft of a surgical tool, and to support at an end thereof the rotary cutting tool of a surgical tool. The monolithic frame is characterized by greater flexibility in opposite directions along a first axis defined normal to the longitudinal axis than in opposite directions along a second axis defined normal to both the first axis and the longitudinal axis.

12 Claims, 5 Drawing Sheets

U.S. PATENT DOCUMENTS

| | | | |
|---|---|---|---|
| 2005/0234477 A1* | 10/2005 | Brown et al. | 606/131 |
| 2006/0004371 A1* | 1/2006 | Williams et al. | 606/80 |
| 2006/0178556 A1* | 8/2006 | Hasser et al. | 600/102 |
| 2007/0093840 A1* | 4/2007 | Pacelli et al. | 606/80 |
| 2010/0030217 A1* | 2/2010 | Mitusina | 606/79 |
| 2010/0057087 A1* | 3/2010 | Cha | 606/80 |
| 2011/0166575 A1* | 7/2011 | Assell et al. | 606/79 |
| 2012/0123196 A1* | 5/2012 | Rion et al. | 600/37 |

* cited by examiner

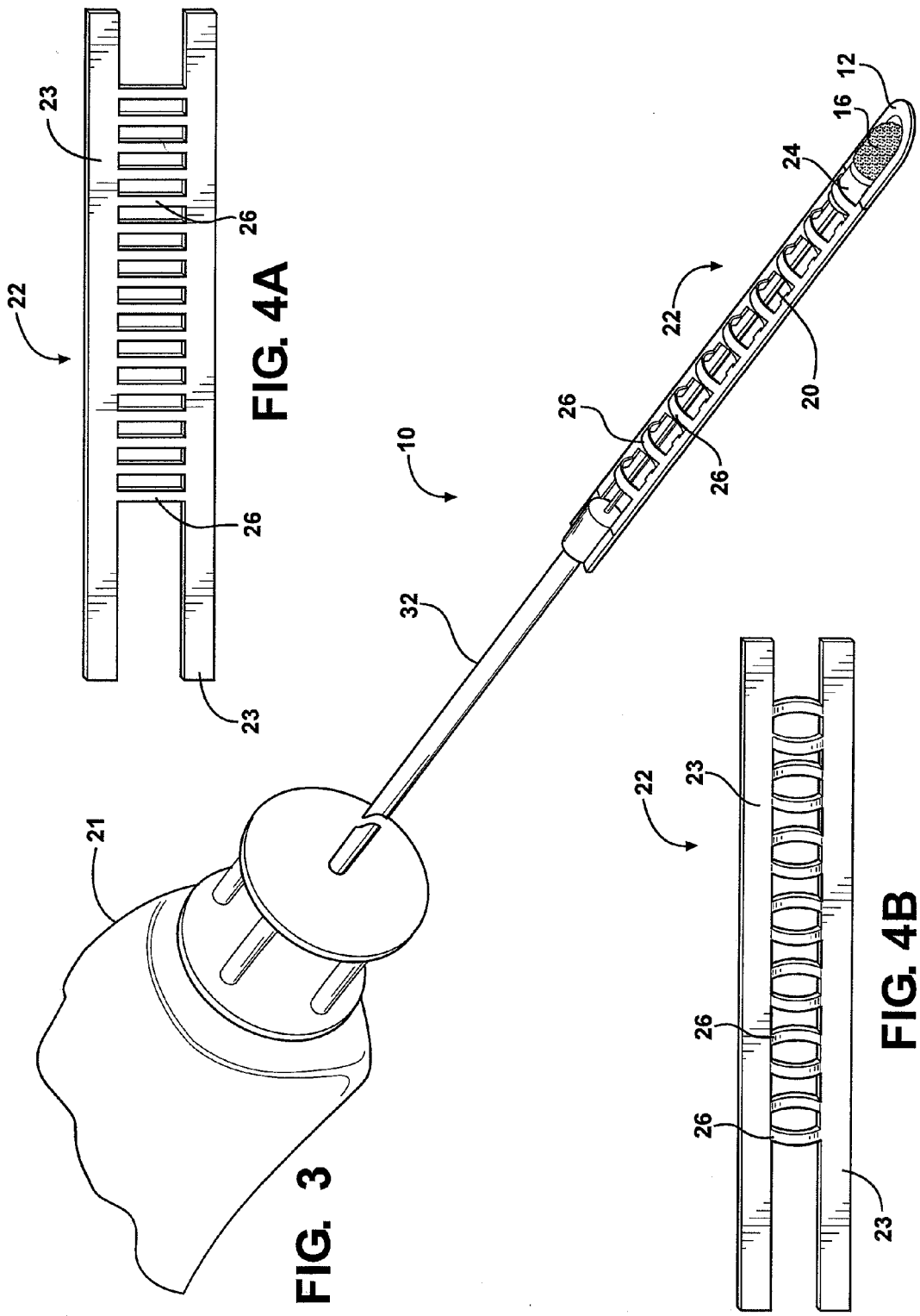

SURGICAL TOOLS AND COMPONENTS THEREOF

RELATED APPLICATIONS

This application is related to, and claims the benefit of priority from, U.S. provisional application Ser. No. 61/044,957, filed Apr. 15, 2008, the disclosure of which provisional application is incorporated herein by reference in its entirety.

FIELD OF THE INVENTION

The subject invention relates to surgical tools and components thereof. More particularly, the invention relates to a surgical tool in which a frame supporting a rotating cutting tool is compliant enough to follow the contours of a bone and/or joint but stiff enough to allow for surface machining of the bone and/or joint.

BACKGROUND OF THE INVENTION

Patients with cartilage-wear, deformations or badly healed fractures often suffer from severe pain during movement. For instance, the current treatment is to fixate the subtalar joint (Talus-Calcaneus). This is accompanied by first removing the cartilage and a layer of bone. The bleeding surfaces are then placed upon each other and the bones are fused. Since the joint surfaces in general and the subtalar joint in particular are three-dimensional curvilinear surfaces, it is difficult to reach the entire joint surface with the current surgical tools and procedures. The current fixation procedure involves the use of a hammer and chisel to remove layers of bone from the joint. The current procedure is, therefore, very challenging, cumbersome and imprecise. Most importantly, the joint shape is not preserved due to lack of proper tools. Often an uneven surface is created, possibly resulting in less surface contact, which in turn causes weaker fixation of the joint.

A compliant cutter in published literature (Tuijthof, et al, "A Compliant Instrument for Arthroscopic Joint Fusion", Proceedings of DETC, ASME Design Engineering Technical Conferences and Computers and Information in Engineering Conferences Salt Lake City, Utah, 2004) works on a similar principle as the subject invention and has a guiding frame, a burr and a multi-piece compliant frame. The frame consists of rings with side wings connected with super-elastic alloy (Nitinol) wires. The cutter was designed for the fusion of the subtalar joint. The authors reported that physical testing of the instrument revealed that it was too flexible and the glued connections between the wires and the rings were not strong enough to hold the components in place. The frame was too flexible to function without adding an additional sleeve. Also, the multi-piece compliant frame consisted of many parts and was difficult to fabricate.

SUMMARY OF INVENTION

The specification discloses a surgical tool and components thereof. The components include a compliant frame for a surgical tool of the type including a flexible drive shaft having disposed at an end thereof a rotary cutting tool, the compliant frame comprising a monolithic frame defining a longitudinal axis between opposite first and second ends thereof, the frame adapted to receive the flexible drive shaft and to support at an end thereof the rotary cutting tool. The monolithic frame is characterized by greater flexibility in opposite directions along a first axis defined normal to the longitudinal axis than in opposite directions along a second axis defined normal to both the first axis and the longitudinal axis.

Per one embodiment thereof, the monolithic frame comprises at least two laterally spaced-apart supports disposed in a common plane and extending parallel to the longitudinal axis, the supports interconnected by a plurality of spaced-apart, transverse ribs, the ribs projecting away from the plane of the supports to define a cage for receiving the flexible drive shaft.

The compliant monolithic frame may be incorporated into a surgical of the type comprising a flexible drive shaft having disposed at an end thereof a rotary cutting tool, the frame receiving therethrough the flexible drive shaft and supporting at an end thereof the rotary cutting tool.

According to one feature of the invention, there may be provided a guide disposed at the first end of the monolithic frame and surrounding at least a portion of the rotary cutting tool. The guide may be separately formed and then secured to the monolithic frame or, according to another embodiment, the guide may be defined by a portion of the monolithic frame.

According to another aspect of the invention, the rotary cutting tool is supported in a bearing.

Further to another feature, there may be provided a sleeve movably disposed over at least part of the monolithic frame. The sleeve is moveable between an extended position in which the sleeve is substantially disposed about the frame and a retracted position in which more of the frame is exposed. Per one feature, the sleeve is biased, such as, for instance, by a spring, to the extended position.

BRIEF DESCRIPTION OF THE FIGURES

The present invention will be appreciated from the following description and accompanying drawings, of which:

FIG. 3 is a perspective view of the surgical tool of FIGS. 1 through 2B;

FIG. 4A is a top-down view of the blank form of the compliant frame according to an exemplary embodiment;

FIG. 4B is a top-down view of the compliant frame formed from the blank of FIG. 4A;

DETAILED DESCRIPTION OF THE INVENTION

Figure 1:
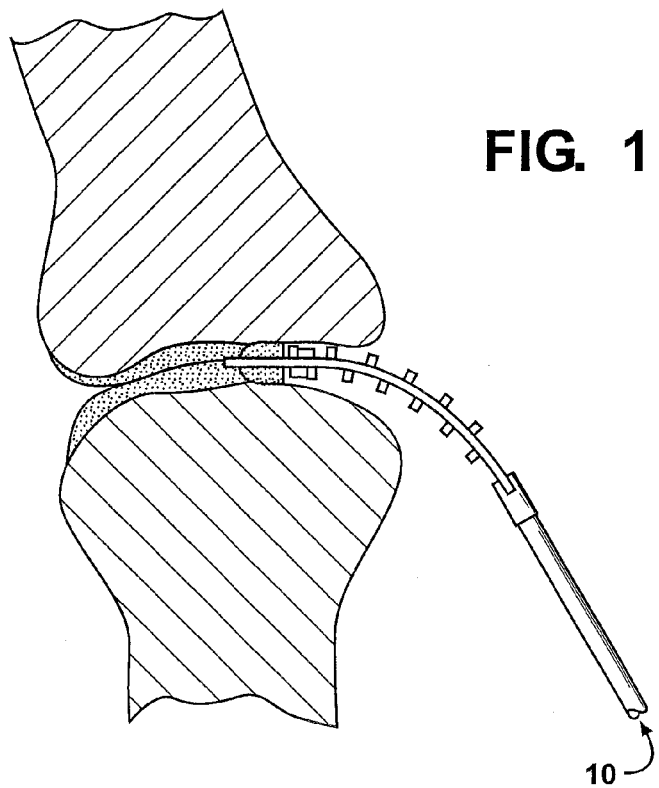
FIG. 1 illustrates the employment of the inventive surgical tool in an exemplary environment.

As required, detailed embodiments of the present invention are disclosed herein. However, it is to be understood that the disclosed embodiments are merely exemplary of the invention, which may be embodied in various and alternative forms. The accompanying drawings are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

Referring now to the drawings, wherein like numerals refer to like or corresponding parts throughout the several views, the invention comprises a compliant frame 22 for a surgical tool of the type including a flexible drive shaft 20 having disposed at an end thereof a rotary cutting tool 16, the frame 22 adapted to receive the flexible drive shaft 20 and to support at an end thereof the rotary cutting tool 16. As explained further herebelow, the frame 22 is characterized by greater flexibility in opposite directions along a first axis Y defined normal to the longitudinal axis X thereof than in opposite directions along a second axis Z defined normal to both the first axis Y and the longitudinal axis X. In this fashion, a surgical tool comprising the frame 22 is defined by both sufficient flexibility so as to be able to follow the shape or contours of the pace between a bone joint, for instance, and relative lateral stiffness so that the surgeon or other user can steer the tool sideways as required to cut away bone material.

Hereafter, the invention is described in the exemplary embodiments thereof in combination with a surgical tool. Such a surgical tool 10 having the compliant frame 22 is shown in FIG. 1 disposed in a joint space between two bones. However, it will be understood that the invention comprehends the compliant frame per se, as well as a surgical tool incorporating the same.

Figure 2A:
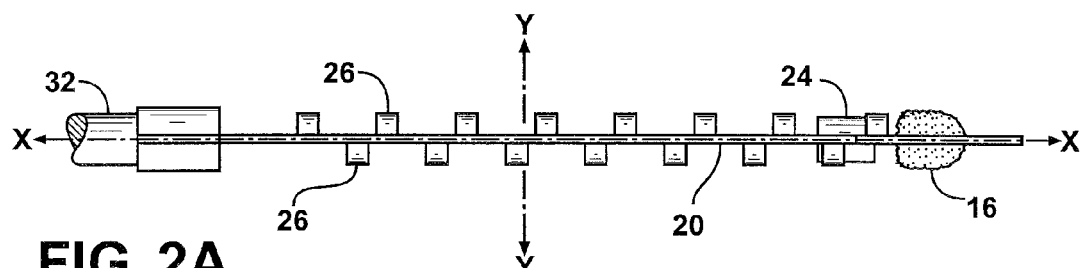
FIG. 2A is a lateral elevation of the compliant frame portion of a surgical tool such as shown in FIG. 1.
Figure 2B:
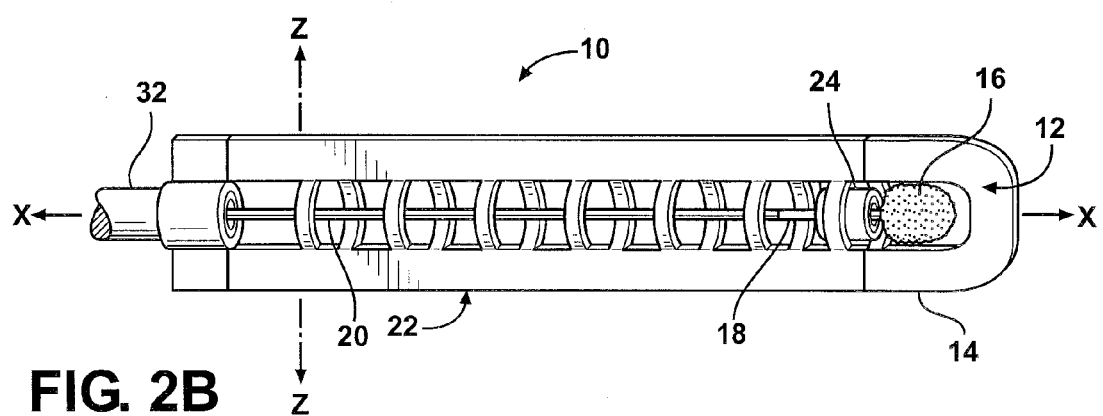
FIG. 2B is a top-down view of the compliant frame portion of FIG. 2A.

Referring to FIGS. 2A, 2B, and 3, the surgical tool 10 of the exemplary embodiment includes flexible drive shaft 20 having disposed at an end thereof the rotary cutting tool 16 (for instance, a burr), and the frame 22 receiving therethrough the flexible drive shaft and supporting at an end thereof the rotary cutting tool 16.

Rotary cutting tool 16 is, more particularly, mounted on a stub axle 18 disposed at an end of the drive shaft 20. A bearing 24 connected to the frame 22 is provided to hold the tool 16 in place and prevent it from moving backwards in a direction away from the guide 12 during the surgical cutting procedure. When the surgical tool 10 is steered sideways or when the instrument bends, the bearing 24 holds the cutting tool 16 in place. At the other end thereof, flexible shaft 20 is connected to a hand-held motor 21.

The compliant frame 22 is connected to a rigid shaft 32 which is supported on the hand-held motor 21. The rigid shaft 32 includes a passageway therein which receives a portion of the flexible drive shaft 20 therethrough.

The flexible drive shaft 20 is constructed in such a way as to provide the necessary flexibility for the operation of the surgical device 10 and also being able to transmit power from the hand-held motor 21 to the cutting tool 16. Per convention, the flexible shaft 20 may, for instance, be constructed of a braided metallic strands, such as braided stainless steel strands, to form a cable. The cutting tool 16 and the axle 18 can be affixed to the flexible drive shaft 20 by various means known to those skilled in the art, including but not limited to, adhesive bonding, soldering, clamping, and mechanical joining.

A guide 12 having leading edge guide surfaces 14 is disposed at an end of frame 22 proximate the rotary cutting tool 16 to passively follow the contour of the joint. The cutting tool 16 follows the direction of the guide surfaces 14 which are controlled directly by the surgeon/user of the tool 10. In the illustrated embodiment, the guide 12 is a separate piece that is affixed to the compliant frame 22. As described further below, however, the guide may also be formed integrally with the frame 22.

Referring also to FIG. 1, in order to reach the entire joint in operation, the surgical tool 10 is inserted, guide 12 first, into a joint and then moved sideways, then forward and then sideways again until the entire joint is reached and/or treated. In order to complete the surface treatment or machining of the joint, the compliant frame 22 must be flexible in opposite directions along the first axis Y so it can follow the shape of the joint and stiffer in opposite directions along the second axis Z (the primary cutting direction) so the surgeon can steer the surgical tool 10 laterally relative to the longitudinal axis X.

In accomplishment of the foregoing, the compliant frame 22 according to the exemplary embodiment comprises at least two laterally spaced-apart supports 23 disposed in a common plane and extending parallel to the longitudinal axis of the frame 22. The supports 23 are interconnected by a plurality of spaced-apart, transverse ribs 26, the ribs projecting away from the plane of the supports to define a cage for the flexible drive shaft 20. As depicted, ribs 26 are each characterized by an arcuate cross-section. Further according to the illustrated embodiment, the ribs 26 more particularly project alternately in opposite directions away from the plane of the supports 23.

Preferably, though not necessarily, the compliant frame 22 is simple to manufacture and low cost so that it can be disposed of at the end of each surgical procedure.

The compliant frame 22 is preferably a monolithic element stamped and/or formed out of surgical grade metal. A suitable biocompatible polymer or other plastic material can also be used to make the compliant frame 22. Depending on the material used for the compliant frame 22, several production methods can be utilized. According to one method, the selected material can be stamped to form the ribs 26 in the final, arcuate shape. Alternatively, the frame 22 may, as described below, be formed as a planar blank which is then deformed into the final, three-dimensional shape herein disclosed. Other methods of fabrication of the compliant, monolithic frame 22 include extrusion, injection molding, pressure die-casting, and powder sintering.

By changing the geometry of the compliant frame 22, the stiffness properties of the compliant frame 22 can be modified. The surgical instrument 10 can thus be tailored for different types of joints to suit different geometric constraints.

The design of the compliant surgical tool 10 lends itself for additional tools to be incorporated, including, by way of non-limiting example, a cooling system, suction, light and a miniature camera.

As noted, the guide 12 can be constructed in different ways other than the specific embodiment shown in FIGS. 2A, 2B and 3. For instance, the elements of the guide 12 can be integrally formed with the compliant frame 22 as illustrated in FIGS. 5A through 6B, further reducing the number of parts or can be a separate piece affixed to the frame 22. The guide 12 can, by way of non-limiting example, be formed during stamping of the compliant frame 22 to form both ribs 26, in the shape of alternating ring-like members, and the guide 12.

Figure 5A:
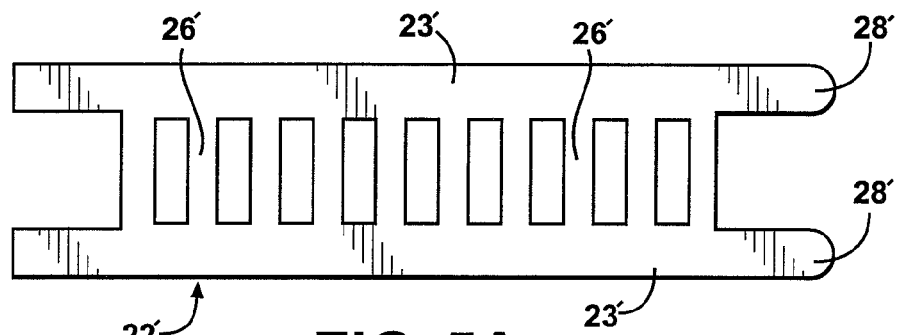
FIG. 5A is a top-down view of the blank form of the compliant frame according to an alternative exemplary embodiment.
Figure 5B:
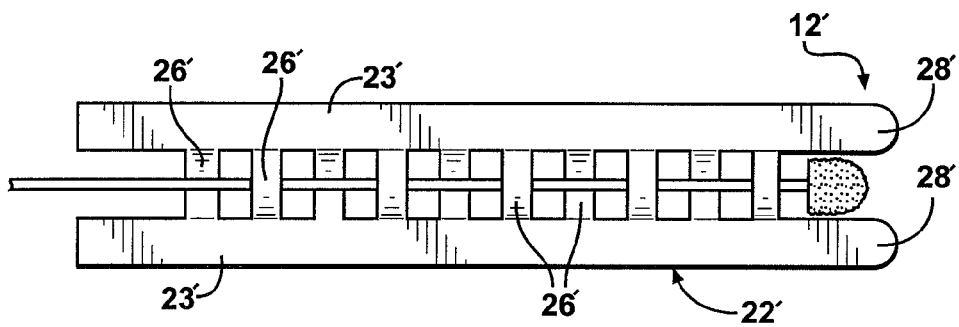
FIG. 5B is a top-down view of the compliant frame formed from the blank of FIG. 5A.

Referring specifically to FIGS. 5A and 5B, there is shown the formation of an open-ended guide 12' defined by the terminal tips 28' of the frame supports 23'. FIG. 5A more particularly depicts the monolithic blank from which the frame 22' is formed, while FIG. 5B depicts the finished frame 22'. As will be appreciated on reference to these figures, as the ribs 26' are formed to project away from the plane of the supports 23', the overall width of the frame 22' is reduced, thereby causing tips 28' to come closer together forming the guide 12'.

Figure 6A:
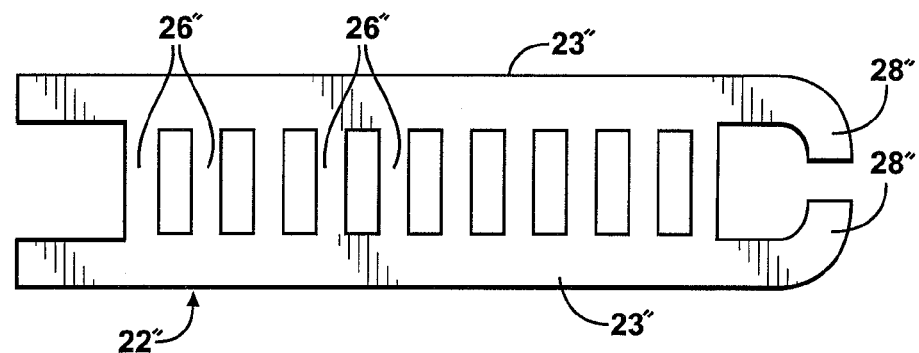
FIG. 6A is a top-down view of the blank form of the compliant frame according to yet another alternative exemplary embodiment.
Figure 6B:
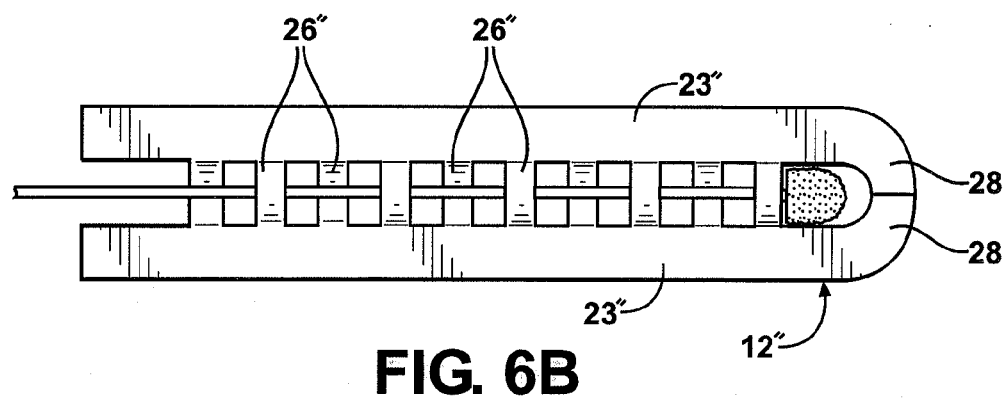
FIG. 6B is a top-down view of the compliant frame formed from the blank of FIG. 6A.
Figure 7A:
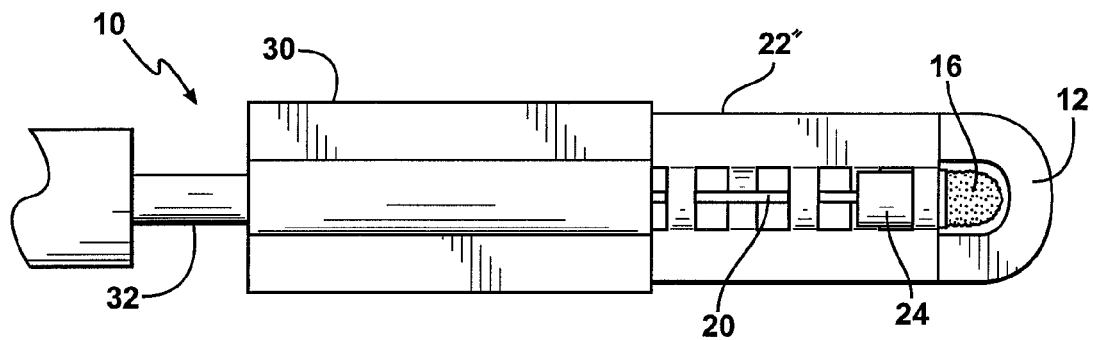
FIG. 7A is a top-down view of a further alternative embodiment of present invention featuring a retractable sleeve.
Figure 7B:
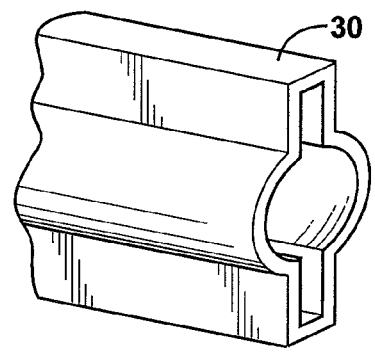
FIG. 7B is a detailed perspective view of the sleeve of FIG. 7A.
Figure 8A:
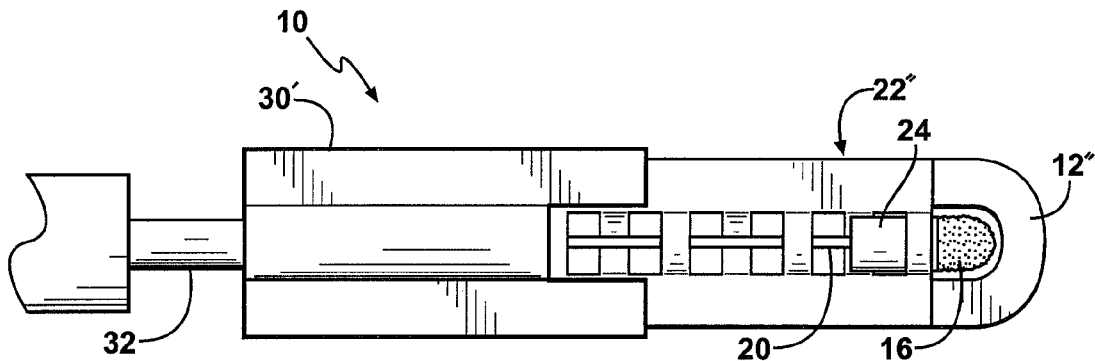
FIG. 8A is a top-down view of an alternative embodiment of the retractable sleeve.
Figure 8B:
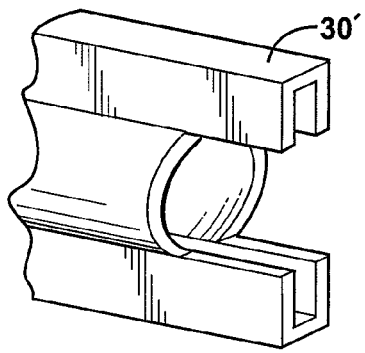
FIG. 8B is a detailed perspective view of the sleeve of FIG. 8A.

Referring specifically to FIGS. 6A and 6B, there is shown the formation of a closed-ended guide 12" defined by the terminal tips 28″ of the frame supports 23″. FIG. 6A more particularly depicts the monolithic blank from which the frame 22″ is formed, while FIG. 6B depicts the finished frame 22″. Substantially as before, as the ribs 26″ are formed to project away from the plane of the supports 23″, the overall width of the frame 22″ is reduced, thereby causing tips 28″ to come together forming the guide 12″.

It is contemplated that guides 12 of different thickness can also be used to suit specific geometry of the bone with which the surgical tool is employed.

An optional retractable sleeve 30 or 30' can be added to the conformable surgical tool 10 as shown in the embodiments of FIGS. 7A through 8B. The retractable sleeve 30 or 30' can be incorporated to prevent any out of plane buckling and to protect the surrounding tissue from any sharp edges of the compliant frame 22. The sleeve 30 or 30' reduces the effective length of the cantilevered tool and prevents any undesirable flexibility (buckling) outside of the patient's joint and extends the rigidity of the surgical tool partially inside the joint. The sleeve 30 or 30', which can be partially inserted in the joint, also helps in keeping the joint open and further stiffens the surgical tool 10 to aid in sideways movement. The length of the inserted part of the sleeve 30 or 30' is limited by the curvature of the joint. The sleeve 30 or 30' can be constructed of any suitable material, such as plastic or metal.

Figure 9A:
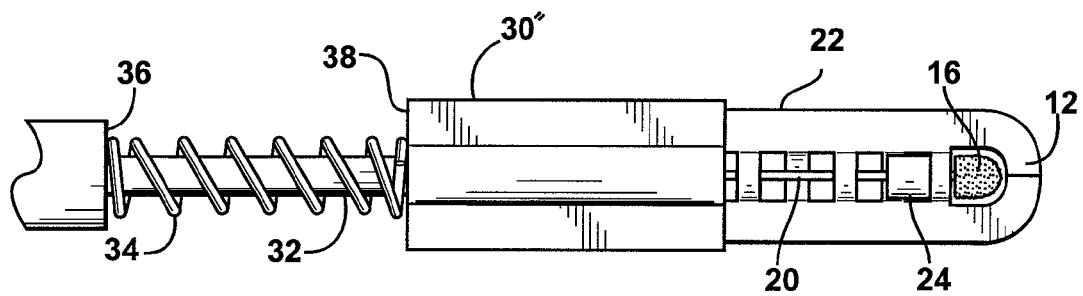
FIGS. 9A and 9B depict two alternative embodiments of the present invention featuring a retractable sleeve with means for biasing the sleeve to the extended position thereof.
Figure 9B:
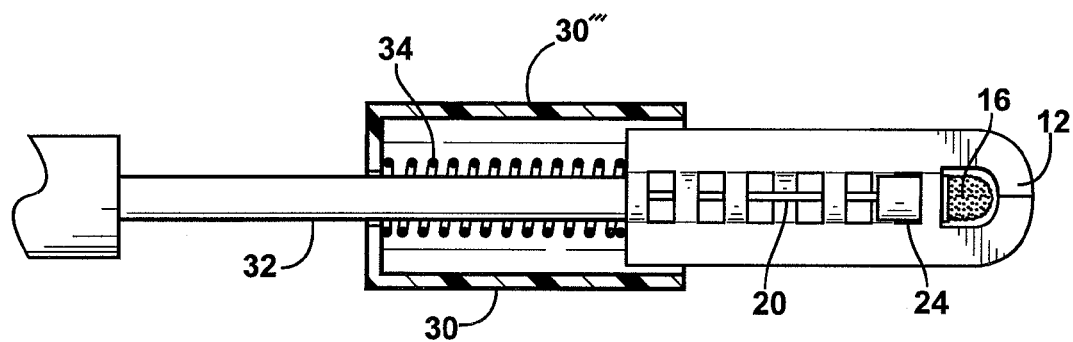

The sleeve can also be biased to the extended position, as shown in FIGS. 9A and 9B. More particularly, such biasing may be provided by a spring 34 disposed about the shaft 32 and outside the sleeve 30″ and abutting against a bearing surface 36 and against an outer portion 38 of the sleeve 30″, as shown in FIG. 9A. Alternatively, the spring 34 can be disposed about the shaft 32 on the inside the sleeve 30″, and attached at one end to the sleeve 30‴ and at its other end to the shaft 32, as shown in FIG. 9B. The spring 34 is preferably formed of a suitable metal or plastic material.

In comparison to the prior art, the subject invention as heretofore described offers numerous advantages, including a compliant frame that can be monolithic instead of comprised of multiple parts with multiple interconnections. According to the exemplary embodiment, the compliant frame is thirteen times stiffer in bending and twenty four times stiffer in lateral displacement as compared to the prior art design described above. Thus, the unitary single-piece compliant frame is appropriately flexible in the cutting direction rather than overly flexible as described in the prior art yet stiff enough to guide the tool sideways in the primary cutting direction without the need for the optional sleeve.

The foregoing description of the exemplary embodiments of the invention have been presented for purposes of illustration and description. They are not intended to be exhaustive or to limit the invention to the precise forms disclosed, and modifications and variations are possible in light of the above teachings or may be acquired from practice of the innovation. The embodiments as shown and described are provided in order to explain the principals of the innovation and its practical application to enable one skilled in the art to utilize the innovation in various embodiments and with various modifications as are suited to the particular use contemplated. Although only a few embodiments of the present invention have been described in detail in this disclosure, those skilled in the art who review this disclosure will readily appreciate that many modifications are possible without materially departing from the novel teachings and advantages of the subject matter recited. Accordingly, all such modifications are intended to be included within the scope of the present invention.

The invention in which an exclusive property or privilege is claimed is defined as follows:

1. A surgical tool, comprising:
    a monolithic frame having a proximal end, a distal end, and a longitudinal axis extending therebetween, the monolithic frame having greater flexibility in opposite directions along a first plane passing through the longitudinal axis than in opposite directions along a second plane passing through the longitudinal axis and normal to the first plane, the monolithic frame having at least two laterally spaced-apart planar supports positioned in the second plane;
    a flexible drive shaft extending within the monolithic frame along the longitudinal axis, the flexible drive shaft having a distal end generally adjacent the distal end of the monolithic frame; and
    a rotary cutting tool coupled to the distal end of the flexible shaft, the rotary cutting tool being supported by the monolithic frame generally adjacent the distal end of the monolithic frame.

2. The surgical tool of claim 1 wherein the monolithic frame comprises a plurality of spaced-apart, transverse ribs extending from one of the at least two laterally spaced-apart planar supports to another of the at least two laterally spaced-apart planar supports, at least some of the plurality of spaced-apart, transverse ribs having arcuate-shaped cross-sections about the longitudinal axis.

3. The surgical tool of claim 2 wherein the at least some of the plurality of spaced-apart, transverse ribs extend in opposing alternating pairs along the at least two laterally spaced-apart planar supports.

4. The surgical tool of claim 1, further comprising a guide disposed at the distal end of the monolithic frame, the guide surrounding at least a portion of the rotary cutting tool.

5. The surgical tool of claim 4 wherein the guide is integrally formed with the monolithic frame at the distal end of the monolithic frame.

6. The surgical tool of claim 4 wherein the guide comprises one or more terminal tips, the one or more terminal tips being planar and coplanar with the at least two laterally spaced-apart planar supports positioned in the second plane.

7. The surgical tool of claim 6 wherein the one or more terminal tips fully surround the rotary cutting tool along the second plane.

8. The surgical tool of claim 1, further comprising:
    a bearing member coupled to the distal end of the monolithic frame, the bearing member having a bearing race rotatably supporting the rotary cutting tool.

9. The surgical tool of claim 1, further comprising:
    a sleeve slidably disposed over at least a portion of the monolithic frame, the sleeve being moveable along at least a portion of the monolithic frame, the sleeve inhibiting the flexibility of the monolithic frame in the first plane and in the second plane.

10. The surgical tool of claim 9, wherein the sleeve is moveable between an extended position in which the sleeve is substantially disposed about the frame and a retracted position in which more of the frame is exposed.

11. The surgical tool of claim 10, wherein the sleeve is biased to the extended position.

12. The surgical tool of claim 11, wherein the sleeve is biased to the extended position by a spring.

\* \* \* \* \*